United States Patent

Hayka et al.

[11] Patent Number: 5,688,118
[45] Date of Patent: Nov. 18, 1997

[54] IMAGE SOUND AND FEELING SIMULATION SYSTEM FOR DENTISTRY

[75] Inventors: Alon Hayka; Liat Eytan, both of Ora, Israel

[73] Assignee: Denx Ltd., Jerusalem, Israel

[21] Appl. No.: 593,300

[22] Filed: Jan. 29, 1996

Related U.S. Application Data

[63] Continuation-in-part of Ser. No. 579,106, Dec. 27, 1995.

[51] Int. Cl.$^6$ .................................................. G09B 23/00
[52] U.S. Cl. .......................... 433/27; 433/27; 433/229; 434/263
[58] Field of Search ................. 433/27, 28, 29, 433/68, 98, 108, 114, 223, 229; 600/117; 434/263

[56] References Cited

U.S. PATENT DOCUMENTS

| | | | |
|---|---|---|---|
| 3,839,797 | 10/1974 | Randolph | 433/27 |
| 4,182,312 | 1/1980 | Mushabac | 433/68 |
| 4,478,580 | 10/1984 | Barrut | 433/223 |
| 4,575,805 | 3/1986 | Moermann et al. | 433/68 |
| 4,824,367 | 4/1989 | Rosenstiel et al. | 433/27 |
| 5,017,139 | 5/1991 | Mushabac | 433/108 |
| 5,163,842 | 11/1992 | Nanomura | 433/114 |
| 5,452,219 | 9/1995 | Dehoff et al. | 433/223 |

FOREIGN PATENT DOCUMENTS 5344980  12/1993  Japan ................................. 433/98

Primary Examiner—Ralph A. Lewis
Attorney, Agent, or Firm—Mark M. Friedman

[57] ABSTRACT

An image, sound and feeling simulation system for dentistry, comprising a dental handpiece having a drill for drilling a cavity in a tooth, the drill having a drilling end; a first three-dimensional sensor attached to the dental handpiece, the first three-dimensional sensor providing the system with position and orientation in space of at least the drill; and a data processing and display unit for simulating of at least the drilling end of the drill. The system further comprising means to control the flow of compressed air operating the drill and thus to control the rotation of the drill to imitate the sound and hand-feeling associated when drilling through tooth layers of different hardness.

23 Claims, 3 Drawing Sheets

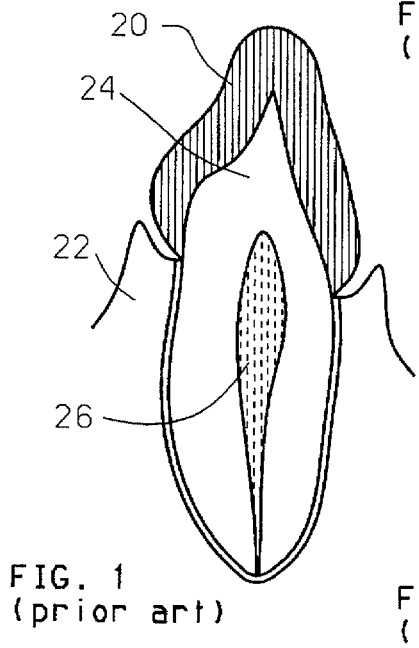
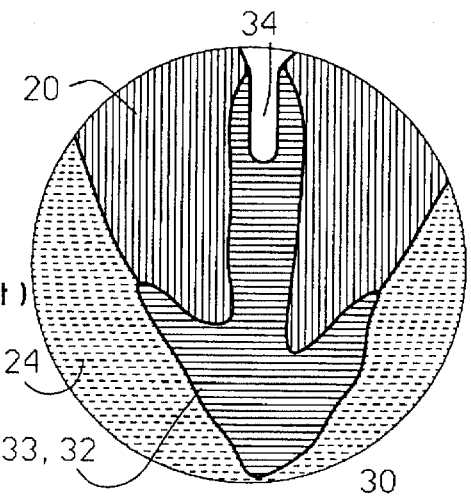
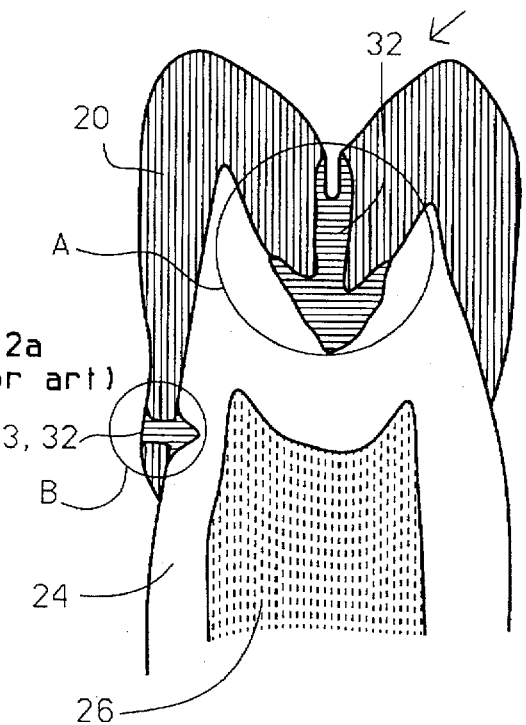
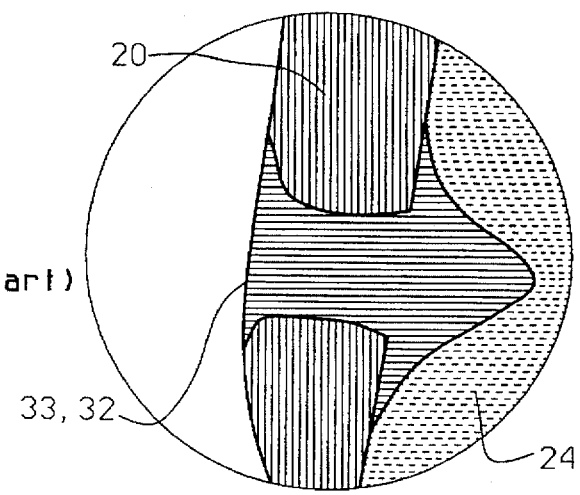
FIG. 1 (prior art)
FIG. 2a (prior art)
FIG. 2b (prior art)
FIG. 2c (prior art)

FIG. 3 (prior art)
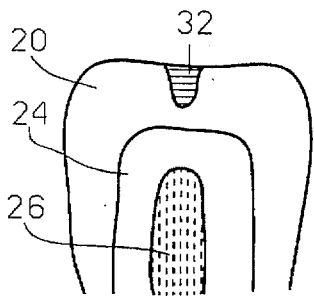
FIG. 3a
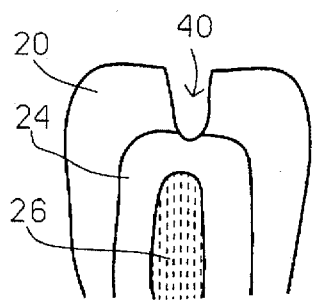
FIG. 3b
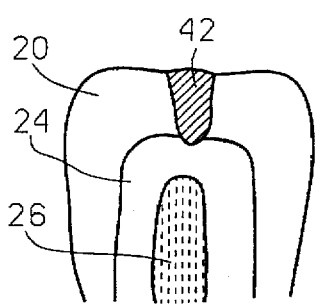
FIG. 3c
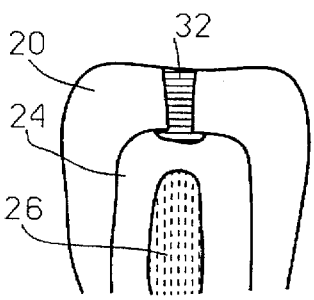
FIG. 3d
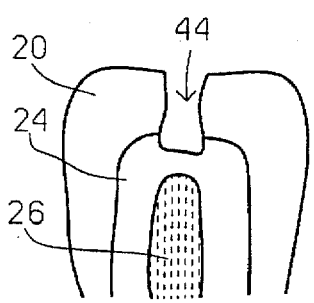
FIG. 3e
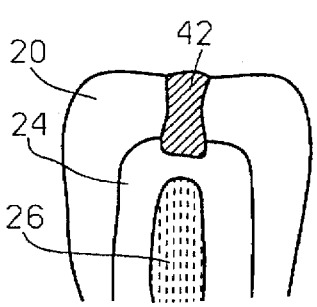
FIG. 3f
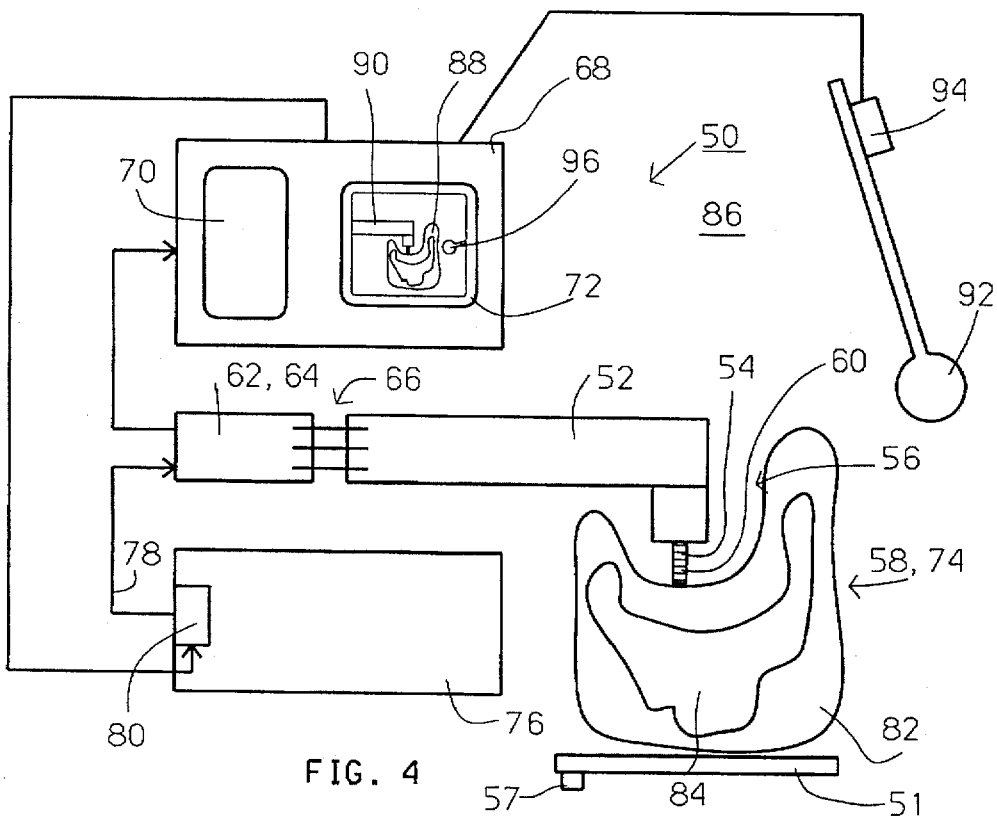
FIG. 4

IMAGE SOUND AND FEELING SIMULATION SYSTEM FOR DENTISTRY

This is a continuation in part of U.S. patent application Ser. No. 08/579,106 filed Dec. 27, 1995, pending.

FIELD AND BACKGROUND OF THE INVENTION

The present invention relates to an image and/or sound and feeling simulation system to be used in the field of dentistry and, more particularly, to a simulation system which can (i) simulate a real process of drilling a tooth during a dental treatment, (ii) imitate a real process of drilling a tooth during training while drilling an artificial tooth and, in both cases, (iii) display the process in an enlarged scale on a display, the system can thus be used for training dentistry trainees as well as to monitor in real-time an actual dental treatment performed by a dentist.

With reference now to FIG. 1, presented is a longitudinal section of a permanent human tooth. As shown in FIG. 1, every permanent tooth includes three major and distinct layers. These are an external enamel layer 20 exposed above the gums 22, an intermediate dentin layer 24 and an internal dental pulp layer 26. Enamel layer 20 is the hard calcified layer of the tooth. Enamel is the hardest tissue in the human body and is very brittle. The thickness of enamel layer 20 varies from individual to individual, from tooth to tooth and, as shown in FIG. 1, also from area to area on a given tooth. It is well known in the art that any impairment to enamel layer 20 by disease or accident can be remedied only by dental restorative treatment, in other words enamel does not regenerate once it has been damaged. The intermediate dentin layer 24 forms the bulk of the tooth and is the second hardest substance in the body. Once destroyed, dentin cannot replace itself in its original form, therefore, desiring dental cavity preparations that remove no more healthy dentin than necessary is crucial. Internal dental pulp layer 16 provides the developmental, protective and sensory mechanisms of the tooth and the nutrients and metabolic processes necessary to sustain the tooth life. As such, this layer includes blood vessels nourishing the tooth and nerves, therefore dental pulp layer 26 is much softer than dentin 24 and enamel 20 layers. Enamel, dentin and dental pulp layers also exist in primary teeth, yet have somewhat different structures.

Dental caries is a common bacterial disease characterized by decalcification of hard tooth structures such as enamel and dentin. The progression of caries through a tooth is exemplified in FIGS. 2a–c. Caries disease can attack the tooth from various directions, two of which are shown in FIGS. 2a–c. FIG. 2a shows an upper part of a tooth 30. As further shown, caries 32 (in black) can attack enamel 20 and dentin 24 layers from above and/or from the side wall of tooth 30. FIG. 2b is an enlargement of circled region A, whereas FIG. 2c is an enlargement of circled region B in FIG. 2a. As clearly observable in FIGS. 2a–c, caries 32 first progresses through enamel layer 20, in some cases generating a hole 34. When caries 32 further progresses and reaches dentin layer 24 it spreads wider and continue towards dental pulp 26 forming an arrow head shape 33. Once caries disease reaches dental pulp 26 the tooth dies and a root canal treatment is to be carded out.

An effective means of stopping the progression of caries into the dental pulp involves removal of all affected tissues (e.g., enamel and dentin), and protecting the tooth by closing thus formed cavity with suitable fillings. Nevertheless, since neither enamel nor dentin can regenerate, it is crucial to minimize the damage to nearby healthy tissues.

The process of forming a cavity in caries affected tooth make use of a dental handpiece, as for example described in U.S. patent application Ser. No. 08/579,106 filed Dec. 27, 1995 (now pending) which is incorporated by reference as if fully set forth herein. A dental handpiece includes a drill for drilling away caries affected tissue(s) and for forming a cavity having a shape most suitable for accommodating a specific filling used, as is further described below.

As mentioned above, during the process of drilling a cavity in a tooth, precaution should be exercised not to remove access of non-regenerated healthy tissue (e.g., enamel and dentin). Referring now to FIG. 3a–f, presented is the process of drilling a cavity in a caries affected teeth. FIGS. 3a–c, present a situation of mild caries 32 disease in which only enamel layer 20 is affected, whereas FIGS. 3d–f present a more severe situation of caries 32 disease, in which both enamel layer 20 and dentin layer 24 are affected. In both situations all affected tissue(s) are to be removed. Referring now to the mild caries situation presented in FIGS. 3a–c, a dentist, aided by a dental handpiece equipped with a drill, drills away affected tissue of enamel 20 and forms a cavity 40. As shown in FIG. 3b, cavity 40 is formed in enamel layer 20, wherein its deepest part positioned at the borderline between enamel layer 20 and dentin layer 24. Referring now to the more severe caries situation presented in FIGS. 3d–f, the dentist, similarly aided by the dental handpiece, drills away affected tissues of both enamel 20 and dentin 24 and forms a deeper cavity 44. As shown in FIG. 3e, cavity 44 is created through enamel layer 20 and into dentin layer 24. Nevertheless, in both mild and severe caries 32 disease, as described above, it is crucial not to remove access healthy dentin. Thus, in the mild case, cavity 40 is not to be drilled into dentin layer 24, whereas in the severe case, drilling into dentin layer 24 is to be exercised cautiously, not to damage dental pulp 26.

As further mentioned above, a cavity drilled in a tooth should have an outline form to match its location in the tooth and the type of filling used to fill thus drilled cavity. Thus for example, a filling of inlays requires a rounded cavity, a filling of ammalgam requires a cavity having less than 90 degrees cavosurface angles, whereas a composite filling attached to the internal walls of the cavity requires a cavity having 90 degrees cavosurface angles.

As mentioned above, caries disease causes decalcification of teeth structures such as enamel and dentin. As further mentioned above, enamel, dentin and dental pulp layers differ in their hardness to a great extent. Thus, when drilling into a tooth using a dental handpiece, at least four types of substances, as classified according to their hardness, are encountered. One type which is the hardest includes healthy enamel, a second type characterized by intermediate hardness is dentin, a third type which is softer than both healthy enamel and dentin is caries affected tissue of either enamel or dentin, whereas a fourth type, which is the softest of all, is the dental pulp layer.

As is understood from the above description, it is crucial to determine presence of dentin when forming a cavity in a treated tooth. This is achieved by monitoring the sound and hand-feeling associated with the drilling process. As mentioned, the drill of a dental handpiece is compressed air operated. Having the drill rotating at a constant speed (e.g., 300,000 rounds per minute) as measured against no resistance (e.g., in the open atmosphere), when drilling through a substance, the rotation speed of the drill decreases as a function of the hardness of the substance. Thus, when a tooth is of concern, the number of rotations per minute is highest when drilling through a dental pulp layer, lower when drilling through caries disease affected dentin and/or enamel, yet lower when drilling through healthy dentin and lowest when drilling through healthy enamel all according to the relative hardness of these substances as described above. Since different rotation speeds of the drill are associated with a different sound and hand-feeling generated, the dentist by listening to the sound and by his feeling can determine weather he is drilling trough the same substance or has he started drilling through a neighboring substance. Furthermore, experienced dentists can determine based on thus produced sound and associated feeling which substance is being drilled at a given moment solely according to the associated sound and feeling. Thus, considering the mild caries disease presented in FIGS. 3a–c, the dentist starts drilling through caries affected enamel 32 which is soft, the drill rotates relatively fast and the associated noise produced is of a relatively high tone. When the drill faces healthy enamel 20 (see FIG. 3a) its rotation is slowed down associated with the generation of a different sound characterized by a lower tone and a different hand-feeling. Thus, the dentist can determine he is now drilling through enamel layer 20. Since it is crucial not to remove access dentin 24, yet it is important to remove all caries affected tissue, the dentist awaits heating an additional sound shift and yet a different feeling, which are associated with drilling through dentin 24. Heating this sound and feeling the associated hand-feeling indicate to the dentist he has reached dentin layer 24 and that he is to be more cautious from now on, to avoid removing access substance from dentin layer 24. Considering now the severe caries disease presented in FIGS. 3d–f, the dentist starts drilling through caries 32 affected enamel and dentin which is soft, the drill rotates relatively fast and the associated noise produced is of a relatively high tone. When the drill faces healthy dentin 24 (see FIG. 3d) its rotation is slowed down associated with the generation of a different sound characterized by a somewhat lower tone and still a different feeling. Thus, the dentist can determine he is now drilling through dentin 24 and exercise extra precaution not to harm dental pulp 26. If however accidentally the drill reaches dental pulp 26 (not shown), the speed of rotation of the drill increases and generates a yet different sound characterized by a high tone and a further different feeling. Thus, the dentist can determine he accidentally harmed pulp 26 and that a root canal treatment is now required.

The profession of dentistry, is based on the wide spectrum of theoretical knowledge which is typically acquired from text books and other publications. Yet, as in other medical fields, a distinct fraction of the knowledge and knowhow involves practical training. While the cost of acquiring trainees with theoretical knowledge by for example lectures and seminars is relatively low, and is effectively performed by lecturers lecturing to a large number of students simultaneously, the cost of practical training is very high. Practical training of dentistry students may be broadly broken down into two successive stages.

During the first stage of practical training (known in the art of dentistry as the pre-clinic or phantom stage) the trainee is taught of the basic manual performance as performed on artificial models or on simple simulators such as ones manufactured by Franz Sachs Co. GmbH, 18 Oberhofer St., Tetmang, Germany. During the second stage of practical training, dentistry students treat actual volunteers supervised by their instructors.

The first stage of practical training involves treating artificial teeth implemented in a mouth of a phantom head imitating a human head. Thus treating artificial teeth involves using a dental handpiece for drilling cavities in the artificial teeth of the phantom head. Nevertheless, artificial teeth are typically made of a synthetic polymer (e.g., plastic) having a given and homogenous hardness (typically that of dentin), therefore it is impossible for a trainee drilling into such an artificial tooth to note sound and hand-feeling shifts as described above, hence the training process fails to appropriately imitate the actual process of drilling into a tooth of a patient. To overcome this problem, a multilayered artificial tooth was developed, the layers are of substances each having a characterizing hardness and are layered as to imitate a real human tooth. Thus, drilling into such a multilayered artificial tooth yields sound and hand-feeling shifts associated with drilling through the various layers and better imitates the real process. Nevertheless, this approach has two major limitations. The first limitation has to do with the fact that the production of multilayered teeth is much more expensive and cumbersome than the production of artificial teeth made of a single substance. It is important to remember in this context that the human mouth has 32 different types of permanent teeth and 20 different types of primary teeth. The second limitation has to do with the fact that in real practice many parameters which are individual specific, tooth specific, caries disease specific (e.g., precise location in a tooth and severity), and selected filling material specific are involved, rendering the approach of using artificial multilayered teeth to imitate various combinations of parameters, impractical.

A majority of a dentist's working area is located within the mouth cavity of the patient. The mouth cavity, however, due to its size and orientation, is not an ideal working area, which results in awkward positions acquired by the dentist during a dental treatment. In the last few decades, technological advancements have brought very noticeable improvements in dental equipment and thus to the dentist's working conditions. Nevertheless, few problems still remained with no satisfactory solution currently available. Furthermore, a drill drilled in a tooth is itself small rendering it difficult to follow and monitor the drilling process and the formation of a suitable cavity.

Thus, the working area of the dentist is limited due to the nature of the work, that is working with one tooth or a portion of a tooth at a time. The dentist's eyes are positioned outside of the mouth of the patient and at a considerable distance from the working area. This, in turn, creates three immediate problems: (i) difficulties in diagnosing small yet important details in the working area; (ii) difficulties in viewing surfaces located at blind spots, known in the art as dead surfaces; and (iii) in order to have a better view of the patient's inner mouth, the dentist is required to lean above the patient.

The first problem above has been partially solved by an expensive magnifying optical device (personal binoculars), adjusted to each user individually.

The second problem is currently solved by a constant use of a dental mirror which is inserted into the mouth of the patient during treatment together with a conventional dental handpiece. Through the mirror, the dentist can see most of the blind spots within the mouth of the patient. Nevertheless, a dental mirror has its own limitations which include: (i) the blind spots appear as an inverted (i.e., mirror) images; (ii) the use of an additional instrument (the mirror) which occupies the dentist's free hand, and the inverted image provided by the mirror results in laborious work requiring a great deal of practice; (iii) the mirror does not always show all of the hidden dimensions of the working area while drilling or grinding, thus causing a noticeable mount of the work to be performed blindly, checked only at the end of the treatment; (iv) since many of the dental treatments involve water being sprayed in the working area, which water function as a coolant while drilling in a tooth and as a catalyst to carry debris from the working area, the mirror becomes wet, the reflected image becomes foggy and thus the vision quality available to the dentist is reduced to an extremely low degree.

A more comprehensive approach of solving all three problems listed hereinabove, which approach also overcomes the above mentioned limitations of the optical device (personal binoculars) and of the dental mirror, is to provide the dental handpiece with an intrinsic imaging system which includes for example a CCD camera and an external screen on which the working area is displayed during the treatment. Devices in accordance with this approach are disclosed, for example, in U.S. Pat. No. 4,858,001 to Milbank et al.; U.S. Pat. No. 5,049,070 to Ademovic; U.S. Pat. No. 5,178,536 to Werly et al.; and U.S. Pat. No. 5,052,924 to Berg. While employing such devices the dentist's working environment is tremendously improved, since these devices enable the dentist to perform a treatment within the patient's mouth while at the same time to observe an enhanced real-time image of the tooth on the screen. The viewing screen can be positioned anywhere, such that a preferred viewing angle may be achieved. Such devices further have the following advantages.

As far as the dentist working conditions are concerned, these devices provide (i) independence upon an external fight source; (ii) greater flexibility for the dentist when positioning himself relative to the mouth of the patient; (iii) no need for a hand-held dental mirror, leaving the dentist's other hand free to simultaneously perform additional duties; and, (iv) obtaining a direct instead of an inverted (i.e., mirror) and, enlarged image of the working area.

As far as the treatment quality is concerned, these devices provide (i) a close-up magnification of the treated area enabling a better view and thus a better detection of the patient's medical condition and a greater ability of monitoring the course of treatment; (ii) an inner view and thus, no blind spots; and, (iii) by enabling the dentist to further remove his/her face from the patients face, the risk of mutual infection with air born pathogens is remarkably lowered.

As far as the patient's comfort level during dental treatment is concerned, these devices provide (i) a lesser need for the patient to widely open his/her mouth during treatment which in some cases is prolonged; and, (ii) a remarked reduction in treatment time.

As far as the patient education and treatment recording are concerned, these devices provide means to record the course of the treatment and to educate the patient of how to better treat (e.g., brush, use a dental floss, etc.) his/her teeth.

However, the devices described in U.S. Pat. No. 4,858, 001 to Milbank et al.; U.S. Pat. No. 5,049,070 to Ademovic; U.S. Pat. No. 5,178,536 Werly et al.; and U.S. Pat. No. 5,052,924 to Berg and others, suffer from the following limitations. First, these and other prior art imaging dental handpieces include a camera implemented within the handle of the dental handpiece, thus, for sterilization purposes, these devices are to be equipped with highly expensive autoclavable cameras. Second, images produced using these devices, present the working area from different angles following the movements imposed by the dentist upon the dental handpiece (and thus the camera) during the dental treatment. The later is a major limitation since while the dentist directly views a patients mouth, the working area is always viewed from a given angle.

U.S. patent application Ser. No. 08/579,106 filed Dec. 27, 1995, (now pending) which is incorporated by reference as if fully set forth herein discloses an imaging dental handpiece which includes a dental handpiece and an imaging system, the imaging system includes a camera which is located in an adapter, itself removably connected to the dental handpiece thus, the camera can be removed prior to sterilization oft he dental handpiece. The imaging system of U.S. patent application Ser. No. 08/579,106 (pending) further includes algorithms to process and display a clear and scaled-up image of a tooth in a patient's mouth, wherein the working area is displayed at a stabilized angle and position at a given treatment time period as if it was directly viewed by a dentist, i.e., from a substantially fixed angle. Thus this system enjoy all advantages of the above mentioned systems yet is not limited by the above described limitations. Nevertheless, this system requires use of a miniaturized video camera which is expensive.

There is thus a widely recognized need for, and it would be highly advantageous to have, a simulation system which can (i) simulate a real process of drilling a tooth during a dental treatment, (ii) imitate a real process of drilling a tooth during training while drilling an artificial tooth and, in both cases, (iii) display the process in an enlarged scale on a display, to be used both for training dentistry trainees and to monitor actual dental treatments performed by a dentist.

SUMMARY OF THE INVENTION

According to the present invention there is provided an image, sound and feeling simulation system to be used in dental clinics and dental phantom laboratories to simulate a real process of drilling a tooth during a dental treatment, imitate the real process of drilling a tooth during training while drilling into an artificial tooth and, in both cases, display the process in an enlarged scale on a display.

According to further features in preferred embodiments of the invention described below, the system comprising (a) a dental handpiece having a drill for drilling a cavity in a tooth, the dill having a drilling end; (b) a three-dimensional sensor having six degrees of freedom attached to the dental handpiece, the three-dimensional sensor providing the system with position and orientation in space of at least the drill; and (c) a data processing and display unit for simulating of at least the drilling end of the drill.

According to still further features in the described preferred embodiments the tooth is an artificial tooth having known shape and dimensions and is located at a fixed known location and orientation in space.

According to still further features in the described preferred embodiments the system further comprising (d) a compressed gas unit being connected via a gas line to the dental handpiece, the dental gas unit providing a compressed gas for rotating the drill, the gas having a flow rate; (e) first means for controlling the flow rate of the gas.

According to still further features in the described preferred embodiments the data processing and display unit includes a set of data, wherein the artificial tooth is simulated as being divided into at least a first simulated region simulating a substance of a first hardness, and a second simulated region simulating a substance of a second hardness, the first hardness is harder than the second hardness; and controls the first means for controlling the flow rate of the gas, such that when the drilling end of the drill is at the first simulated region the drill rotates in a first speed, whereas when the drilling end of the drill is at the second simulated region the drill rotates in a second speed, the first speed is slower than the second speed.

According to still further features in the described preferred embodiments the artificial tooth is simulated as being divided into at least a first simulated region simulating a substance of a first hardness and a second simulated region simulating a substance of a second hardness, the first hardness is harder than the second hardness, wherein, atmosphere surrounding the artificial tooth is simulated as being a third region of no hardness. The processing and display unit controls the first means for controlling the flow rate of the gas, such that when the drilling end of the drill is at the first simulated region the drill rotates in a first speed, when the drilling end of the drill is at the second simulated region the drill rotates in a second speed, and when the drilling end of the drill is at the third simulated region the drill rotates in a third speed, the first speed is slower than the second speed, itself slower than the third speed.

According to still further features in the described preferred embodiments the tooth is an artificial tooth having known shape and dimensions and is located on a platform, the system further comprising an additional three-dimensional sensor being attached to the platform, the additional three-dimensional sensor providing the system with position and orientation in space of the artificial tooth. In this case, the data processing and display unit includes a first set of data including the shape and dimensions of the artificial tooth, the first set of data further including the location and orientation in space of the artificial tooth as received from the additional three-dimensional sensor; receives a second set of data including the position and orientation in space of at least the drilling end of the drill from the three-dimensional sensor; calculates the effect of the position and orientation in space of the drilling end of the drill on the shape of the artificial tooth; and displays a simulation of the shape of the artificial tooth, such that a user monitors the effect of the drill on the shape of the artificial tooth by viewing the displayed simulation.

According to still further features in the described preferred embodiments the system further comprising a dental mirror and a yet additional three-dimensional sensor, the yet additional sensor being attached to the dental mirror and providing the system with position and orientation in space of the dental mirror, wherein the data processing and display unit receives a third set of data including the position and orientation in space of the dental mirror, from the yet additional three-dimensional sensor, the data processing and display unit displays a simulation of the dental mirror in space and of a simulated reflection reflected from the displayed simulation of the dental mirror.

According to still further features in the described preferred embodiments the tooth is of a patient and having known shape, dimensions and internal distribution of enamel, dentin and caries affected tissue, the system further comprising (d) a still additional three-dimensional sensor attached to the head of the patient, the still additional three-dimensional sensor providing the system with the position and orientation in space of the tooth, the still additional three-dimensional sensor and the known shape, dimensions and internal distribution of enamel, dentin and caries affected tissue of the tooth being for simulating the tooth by the data processing and display unit, such that a user is capable of monitoring the drilling of the cavity in the tooth.

According to still further features in the described preferred embodiments any of the three-dimensional sensors are selected from the group consisting of electromagnetic based three-dimensional sensors, ultrasound based three-dimensional sensors, optic based three-dimensional sensor and mechanical three-dimensional sensors.

According to still further features in the described preferred embodiments the compressed gas unit is a compressed air unit and the gas is air.

According to still further features in the described preferred embodiments the simulation is scaled-up.

According to still further features in the described preferred embodiments the platform is a phantom head imitating a head of a human.

BRIEF DESCRIPTION OF THE DRAWINGS

The invention herein described, by way of example only, with reference to the accompanying drawings, wherein:

FIG. 1 is a longitudinal section through a tooth, presenting the tooth layers and structures;

FIG. 2a–c is a presentation of caries disease affecting tooth tissues;

FIG. 3a–f is a presentation of a cavity forming and filling processes in teeth affected with mild and severe caries during a dental treatment of a patient;

FIG. 4 is a schematic depiction of an image, sound and feeling simulation system for dentistry according to the present invention

DESCRIPTION OF THE PREFERRED EMBODIMENTS

Figure 5:
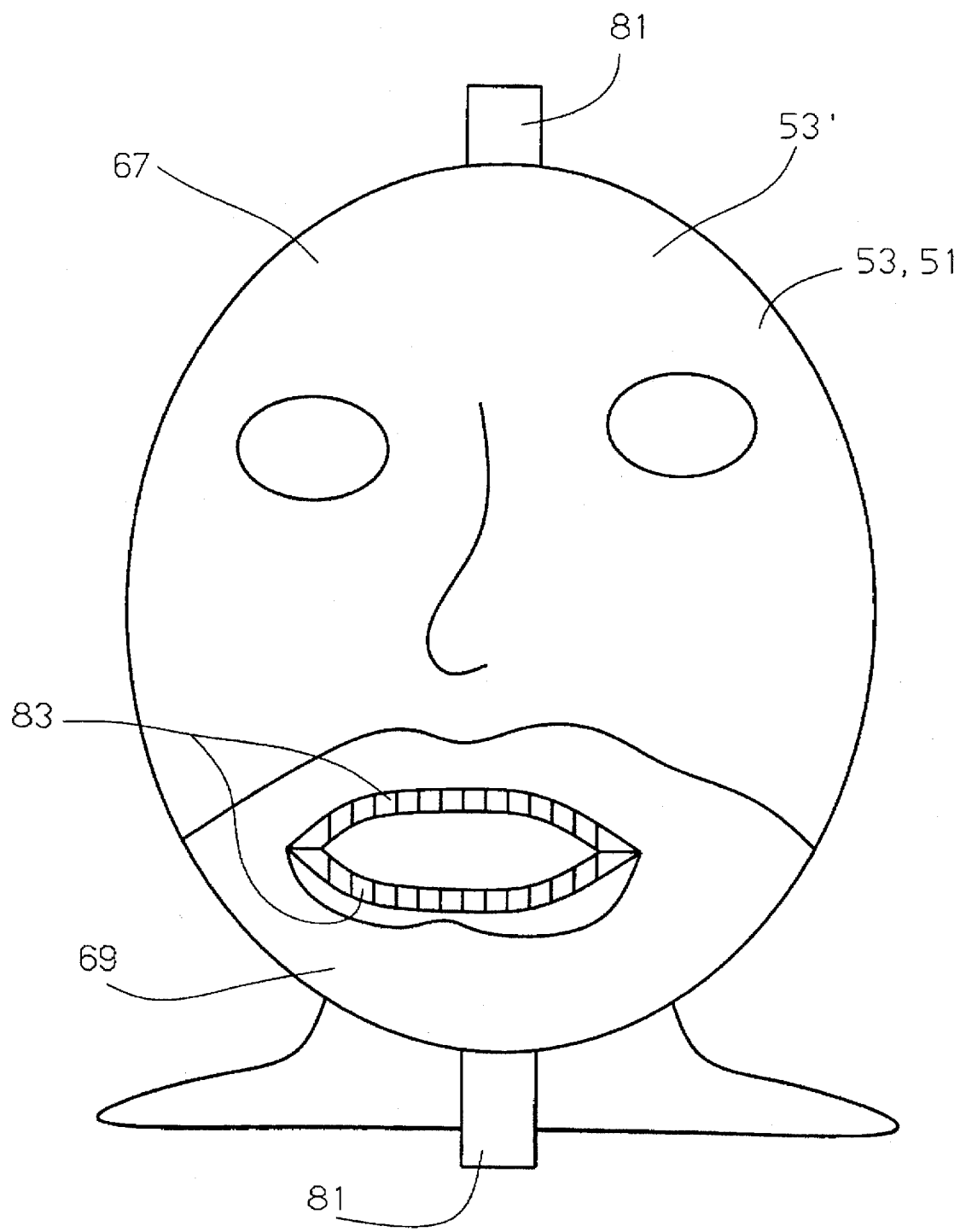
FIG. 5 is a schematic view of a human head, which is used herein to indicate a real head and a phantom head.

The present invention is of an image, sound and feeling simulation system to be used in the field of dentistry which can be used to simulate a real process of drilling a tooth during a dental treatment, imitate a real process of drilling a tooth during training in drilling an artificial tooth and, in both cases, display the process in an enlarged scale on a display. Specifically, the present invention can be used for training dentistry trainees as well as to monitor in real-time an actual dental treatment performed by a dentist.

The principles and operation of a simulation system according to the present invention may be better understood with reference to the drawings and accompanying descriptions.

Referring now to the drawings, FIG. 4 schematically illustrates the simulation system of the present invention refereed hereinbelow as system 50. System 50 includes various configurations as is detailed below. Nevertheless, it should be noted that these configurations may be combined to yet additional and more complex configurations. Various configurations of system 50 may serve different functions. Basically, system 50 is to simulate a treated tooth either of a patient or artificial and to further simulate at least a drill of a dental handpiece drilling into the tooth. When system 50 is used to train dentistry trainees drilling into an artificial tooth (typically made of a substance having a characterizing and homogenous hardness), system 50 preferably further control the speed in which the drill rotates as a function of the position and orientation of the drilling end of the drill relative to the tooth, thus imitating a real situation wherein the tooth is made of substances each having its characterizing hardness.

Thus, with reference now to FIG. 4, in a minimal configuration system 50 includes a dental handpiece 52 having a drill 54 for drilling a cavity 56 in a tooth 58, drill 54 is equipped with a drilling end 60. System 50 according to its minimal configuration further includes a first three-dimensional sensor 62 attached to dental handpiece 52, sensor 62 providing system 50 with information regarding the position and orientation in space of at least drilling end 60 of drill 54. Sensor 62 may be selected from various types functioning according to various principles. Sensor 62 is preferably attached to handpiece 52 through an adapter 64 itself removably connected at rear end 66 of dental handpiece 52. Thus attaching sensor 62 to handpiece 52 enables to sterilize handpiece 52 after removing both adapter 64 and sensor 62.

The term 'three-dimensional sensor' as used herein in this document and especially in the claims section below refers to sensors capable of providing information regarding the position (e.g., in X, Y and Z terms of a Cartesian coordinates system) and the orientation (e.g., in $\alpha, \beta$ and $\gamma$ angles of the Cartesian coordinates system or as also known in the art as azimuth, elevation and roll) of an element in space, that is providing information regarding the position and orientation of an element in space in six degrees of freedom.

Three-dimensional sensors can be broken into mechanical and nonmechanical sensors. It should be noted that most non-mechanical three-dimensional sensors are systems including at least two separated parts wherein the first part is attached to an element to be three-dimensionally monitored and the second part is stationary. The two separated parts communicate such that the position and orientation in space of the element can be determined. On the other hand, mechanical three-dimensional sensors typically include arms connected with suitable joints. One of the arms is attached to the element to be threedimensionally monitored and suitable detectors typically implemented at the joints report of relative arms movement such that if a reference position and orientation in space are priorly defined for the element, its position and orientation can be monitored and determined relative to the reference state. Mechanical sensors of other types (e.g., employing vibrated membranes) are also known. Thus, when the phrase 'three-dimensional sensor being (or is) attached to' an object (e.g., a dental handpiece), is used herein in this document and especially in the claims below, then, if a non-mechanical sensor having two parts as described above is of choice, the phrase meaning is that the first part is either directly or indirectly attached to the object, wherein the second part is preferably stationary positioned elsewhere, whereas if a mechanical sensor is of choice, since it is typically an integral apparatus, the phrase meaning is that the mechanical sensor is either directly or indirectly (e.g., via a secondary connector) attached to the object. It will be however appreciated that any type of three-dimensional sensor(s) having six degrees of freedom is suitable for use in the system of the present invention.

Suitable mechanical three-dimensional sensors are for example ones manufactured by Immersion Corp., ems: immersion@srarconn.com. and ones manufactured by Shooting Star Technology, 52023 Yale Rd., Rosedale, Canada. Suitable non-mechanical three-dimensional sensors may be divided to subcategories according to their mode of operation. Thus, non-mechanical three-dimensional sensors include for example (i) electromagnetic field based' sensors such as ones manufactured by Polhemus, Colchester Vt., and Ascension Technology Corp. Burlington Vt.; (ii) ultrasound based sensors; and (iii) optic based sensors such as ones manufactured by Adaptive Optics Associates, Inc., Cambridge, Mass.

System 50 according to its minimal configuration further includes a data processing and display unit 68 for simulating of at least drilling end 60 of drill 54. Unit 68 includes a suitable processor 70 such as a PC computer equipped with suitable algorithms and unit 68 further includes display means such as a monitor 72.

According to some preferred configurations, system 50 is used to train dentistry trainees. In this case system 50, image wise, sound wise and associated hand-feeling Wise, simulates a process of drilling into a 'real' tooth while in fact drilling into an artificial tooth 58 which is typically made of a substance 74 of a s given hardness. According to one configuration tooth 58 has known shape and dimensions and is located at a fixed known location and orientation in space. According to this configuration, system 50 further includes a compressed gas unit 76 connected via a gas line 78 either directly or via adapter 64 to dental handpiece 52. Dental gas unit 76 providing a compressed gas for rotating drill 54. Further according to this configuration, system 50 further includes first means 80 for controlling the flow rate of the gas as follows. Data processing and display trait 68 includes a set of data in which artificial tooth 58 is simulated as being divided into at least a first simulated region 82 simulating a substance of a first hardness (e.g., enamel), and a second simulated region 84 simulating a substance of a second hardness (e.g., dentin), the first hardness is harder than the second hardness. Furthermore, Data processing and display unit 68 controls first means 80, such that when drilling end 60 of drill 54 is at first simulated region 82, drill 54 rotates in a first speed, whereas when drilling end 60 of drill 54 is at second simulated region 84, drill 54 rotates in a second speed, the first speed is slower than the second speed. Thus, both sound and hand-feeling are changed while the rotation speed of drill 54 changes, although drill 54 faces a substantially constant resistance enforced by substance 74 of which artificial tooth 58 is made. It is clear to one ordinarily skilled in the art that similarly, artificial tooth 58 may be divided into additional simulated regions characterized by yet additional level of hardness, e.g., s to simulate a caries disease affected tissue or a dental pulp layer (not shown). As well known in the art of dentistry, compressed gas unit is typically a compressed air unit, wherein the compressed gas is compressed air. In a preferred embodiment atmosphere 86 surrounding artificial tooth 58 is simulated as being a third region of no hardness. In this case Data processing and display unit 68 controls first means 80, such that when drilling end 60 of drill 54 is at first simulated region 82, drill 54 rotates in a first speed, when drilling end 60 of drill 54 is at second simulated region 84, drill 54 rotates in a second speed, and when drilling end 60 of drill 54 is at third simulated region 86, drill 54 rotates in a third speed, the first speed is slower than the second speed, itself slower than the third speed. Since the speed of rotation of drill 54 dictates the sound and hand-feeling associated with its rotation, a sound and hand-feeling simulation of drilling a 'real' tooth, having layers and structures of different hardness, is thus formed.

According to yet another configuration, data processing and display unit 68 lo of system 50 (i) includes a first set of data including the shape, dimensions and fixed location and orientation in space of artificial tooth 58; (ii) receives a second set of data including the position and orientation in space of at least drilling end 60 of drill 54, from first three-dimensional sensor 62; (iii) calculates the effect of the position and orientation in space of drilling end 60 of drill 54 on the shape of artificial tooth 58; and (iv) displays a simulation 88 of the shape of the artificial tooth, such that a user monitors the effect of drill 54 on the shape of artificial tooth 58 by viewing displayed simulation 88 as presented on monitor 72. In a preferred embodiment simulation 88 is scaled up and also includes additional simulated features 90 such as of dental handpiece 52.

In still another preferred configuration, system 50 alternatively or further includes a dental mirror 92 and a second three-dimensional sensor 94 attached to dental mirror 92 and providing the system with the position and orientation in space of dental mirror 92, wherein data processing and display unit 68 receives a third set of data including the position and orientation in space of dental mirror 92, from second three-dimensional sensor 94, data processing and display unit 68 displays a simulation 96 of dental mirror 92 in space and of a simulated reflection reflected from the displayed simulation of dental mirror 92. It is clear to one ordinarily skilled in the art that any of the above described three-dimensional sensors can provide the functionality of second sensor 94. Thus, according to this configuration a full simulation of the drilling process into artificial tooth 58 is accomplished.

According to still another preferred configuration, artificial tooth 58 is located on a platform 51, system 50 further includes a third three-dimensional sensor 57, attached to platform 51, third three-dimensional sensor providing the system with the position and orientation in space of artificial tooth 58, wherein the first set of data including the shape and dimensions of artificial tooth 58, and the location and orientation in space of artificial tooth 58, as received from third three-dimensional sensor 57. It is clear to one ordinarily skilled in the art that any of the above described three-dimensional sensors can provide the functionality of the, third sensor. In a preferred embodiment, as shown in FIG. 5, platform 51 is a phantom head imitating a head 53 of a human.

As mentioned hereinabove, various configurations of system 50 may serve different functions. Basically, system 50 is to simulate a treated tooth either of a patient or artificial and a drill of a dental handpiece drilling into the tooth. The following configurations refer to the use of system 50 for simulation of drilling into a tooth of a patient (i.e., a 'real' tooth) as performed by a dentist in a dental clinic. For this purpose system 50 components described under its minimal configuration above are employed, yet the system further includes data regarding the shape, dimensions and internal distribution of enamel, dentin and caries affected tissue(s) in the treated tooth, as is determined for example by combining X-ray and/or MRI information with visual (e.g., video) information as can be derived for example using the imaging dental-handpiece of U.S. patent application Ser. No. 08/579, 106 (pending). According to this configuration, as shown in FIG. 5, now serving to illustrate a head of a patient 53' system 50 further includes a three-dimensional sensor 81 attached to the head of the patient (preferably to the skill 67 or lower jaw, 69 and providing system 50 with the position and orientation in space of the treated tooth 83 three-dimensional sensor 81 and the known shape, dimensions and internal distribution of enamel, dentin and caries affected tissue of tooth 83 enable system 50 to simulate tooth 83 data processing and display unit 68, such that the dentist is capable of monitoring the drilling process of the cavity in tooth 83. As before, the simulation is preferably scaled-up, the additional sensor 81 is preferably any of the above mentioned ones, and a simulation of a dental mirror as described above is also preferred.

Hence, the system according to the present invention provides dentistry trainees with sound, image and feeling simulations associated with a real cavity forming process, whereas the system is also suitable for providing a dentist with real time scaled-up simulated image of the cavity forming process in a tooth of a patient. A major advantage of the system according to the present invention is that for image simulation, the system does not involve a miniaturized camera and is therefore less costly.

For training purposes, the system is preferably equipped with data for sound, feeling and image simulation of various parameters such as the type of tooth being drilled, thickness of layers within the moth, location of caries disease affected tissues within the tooth, severity of caries disease and many other parameters differing from case to case in real practice. For example consider the selectable parameters of Table 1 below.

TABLE 1

| Parameter: | Options: |
| --- | --- |
| Dentition | permanent, primary |
| Tooth | 32 permanent teeth in adults, 20 primary teeth in children |
| Cavity class | class 1, class 2 MO, class 2 DO, class 2 MOD, class 3 class 4, class 5 B, class 5 L |
| Cavity depth | superficial, medium, deep |
| Cavity extension | narrow, medium, wide |
| Filling | ammalgam, composite, inlay, preventive, restorative |

Thus, a system which can simulate practically endless number of different situations is readily available.

As is clear to one skilled in the art, the various configurations of the system thus described enable a dentistry trainee to perform all variations of all dental procedures such as cavity preparations, crown preparations, root canal preparations and all other performances carried out by means of the dental handpiece and/or other dental-handtools (e.g., a chisel, an angle former, an enamel hatchet, etc.). Furthermore, in case of operative dentistry training, the user may select a tooth he would like to practice on, the extent of caries, and the type, depth and shape of cavity to be prepared. The actual work with the system is preferably performed in a phantom head's mouth and is displayed and observed by the trainee on the screen. Preferably all parameters of cavity preparation are monitored, analyzed and displayed in real time, thus, leading the trainee to learn the ideal performance on a dental cavity. Furthermore, using the system of the present is invention, the trainee is able to review all the stages of his work, to identify all the mistakes made, to compare his performances with an ideal cavity preparation to be simultaneously displayed and to improve his skill in the art. The system of the present invention may be operated by drilling in artificial teeth or by virtual drilling. The system further presents the following advantages: (i) using the system, the space required for training stages will be significantly reduced; (ii) using the system, the number of instructors required will be sharply decreased; (ii) using the system, the vast majority of instructed teaching will change to simulated self teaching; (iv) using the system, the ability to repeat exercises will be unlimited without increasing costs; (v) using the system, graphic demonstration of all dental procedures will be included in one teaching system; (vi) using the system, will provide complete standardization of all procedures; (vii) using the system, the performance of the exercise is under control and feedback;

(viii) using the system, the users will be able to adjust the computed exercises to their teaching methods and needs; (ix) using the system, the self teaching will not be limited to formal teaching hours; (x) using the system, continuous evaluation of student's performance in real time can be provided, which can serve as an assessment and examination tool; (xi) using the system, the ability to train under a wide range of rare dental conditions will be readily available; (xii) using the system, the student will gain improved manual dexterity before approaching patients; (xiii) using the system, the overall cost and duration of student training will be reduced; and most importantly, (xiv) using the system, the graduate trainee will attain a higher standard of performance and knowledge in comparison with trainees practicing conventional methods.

While the invention has been described with respect to a limited number of embodiments, it will be appreciated that many variations, modifications and other applications of the invention may be made.

What is claimed is:

1. A simulation system for dentistry, comprising:
a hand-held dental handpiece having a drill for drilling a cavity in an artificial tooth having known shape and dimensions and being located at a fixed known location and orientation in space, said drill having a drilling end, said dental handpiece being shaped and dimensioned suitable to be held by the hand of a user:

(b) a first three-dimensional sensor attached to said dental handpiece, said first three-dimensional sensor providing the system with position and orientation in space of at least said drill;

(c) a data processing and display unit for receiving data about said position and orientation in space of at least said drill from said first three dimensional sensor, for simulating said drill;

(d) a compressed gas unit being connected via a gas line to said dental handpiece, said gas unit providing a compressed gas for rotating said drill, said gas having a flow rate; and (e) first means for controlling said flow rate of said gas; wherein said data processing and display unit:

(i) includes a set of data, wherein said artificial tooth is simulated as being divided into at least a first simulated region simulating a substance of a first hardness, and a second simulated region simulating a substance of a second hardness, said first hardness is harder than said second hardness; and (ii) controls said first means for controlling said flow rate of said gas, such that when said drilling end of said drill is at said first simulated region said drill rotates in a first speed, whereas when said drilling end of said drill is at said second simulated region said drill rotates in a second speed, said first speed is slower than said second speed.

2. A simulation system for dentistry as in claim 1, wherein said first three-dimensional sensor is selected from the group consisting of an electromagnetic based three-dimensional sensor, an ultrasound based three-dimensional sensor, an optic based three-dimensional sensor and a mechanical three-dimensional sensor.

3. A simulation system for dentistry as in claim 1, wherein said compressed gas unit is a compressed air unit and said gas is air.

4. A simulation system for dentistry as in claim 1, wherein the simulation is scaled-up.

5. A simulation system for dentistry comprising:

(a) a hand-held dental handpiece having a drill for drilling a cavity in an artificial tooth having known shape and dimensions and being located at a fixed known location and orientation in space, said drill having a drilling end, said dental handpiece being shaped and dimensioned suitable to be held by the hand of a user:

(b) a first three-dimensional sensor attached to said dental handpiece, said first three-dimensional sensor providing the system with position and orientation in space of at least said drill:

(c) a data processing and display unit for receiving data about said position and orientation in space of at least said drill from said first three dimensional sensor, for simulating said drill:

(d) a compressed gas unit being connected via a gas line to said dental handpiece, said gas unit providing a compressed gas for rotating said drill, said gas having a flow rate; and (e) first means for controlling said flow rate of said gas; wherein said data processing and display unit:

(i) includes a set of data, wherein said artificial tooth is simulated as being divided into at least a first simulated region simulating a substance of a first hardness and a second simulated region simulating a substance of a second hardness, said first hardness is harder than said second hardness, wherein, atmosphere surrounding said artificial tooth is simulated as being a third region of no hardness; and (ii) controls said first means for controlling said flow rate of said gas, such that when said chilling end of said drill is at said first simulated region said drill rotates in a first speed, when said drilling end of said drill is at said second simulated region said drill rotates in a second speed, and when said drilling end of said drill is at said third simulated region said drill rotates in a third speed, said first speed is slower than said second speed, itself slower than said third speed.

6. A simulation system for dentistry comprising:

(a) a hand-held dental handpiece having a drill for drilling a cavity in an artificial tooth having known shape and dimensions and located at a fixed known location and orientation in space, said drill having a drilling end, said dental handpiece being shaped and dimensioned suitable to be held by the hand of a user;

(b) a first three-dimensional sensor attached to said dental handpiece, said first three-dimensional sensor providing the system with position and orientation in space of at least said drill: and (c) a data processing and display unit for receiving data about said position and orientation in space of at least said drill from said first three dimensional sensor, for simulating said drill;

wherein said data processing and display unit:

(i) includes a first set of data including said shape, dimensions and fixed location and orientation in space of said artificial tooth;

(ii) receives a second set of data including said position and orientation in space of at least said drilling end of said drill, from said first three-dimensional sensor:

(iii) calculates the effect of said position and orientation in space of said drilling end of said drill on said shape of said artificial tooth; and (iv) displays a simulation of said shape of said artificial moth, such that a user monitors said effect of said drill on said shape of said artificial tooth by viewing said displayed simulation;

the system further comprising a dental mirror and a second three-dimensional sensor, said second sensor being attached to said dental mirror and providing the system with position and orientation in space of said dental mirror, wherein said data processing and display unit receives from said second three-dimensional sensor a third set of data, said third set of data includes said position and orientation in space of said dental mirror, said data processing and display unit displays a simulation of said dental mirror in space and of a simulated reflection reflected from said displayed simulation of said dental mirror.

7. A simulation system for dentistry as in claim 6, wherein any of said first and second three-dimensional sensors are selected from the group consisting of electromagnetic based three-dimensional sensors, ultrasound based three-dimensional sensors, optic based three-dimensional sensors and mechanical three-dimensional sensors.

8. A simulation system for dentistry comprising:
(a) a hand-held dental handpiece having a drill for drilling a cavity in an artificial tooth having known shape and dimensions and located at a fixed known location and orientation in space, said drill having a drilling end, said dental handpiece being shaped and dimensioned suitable to be held by the hand of a user:
(b) a first three-dimensional sensor attached to said dental handpiece, said first three-dimensional sensor providing the system with position and orientation in space of at least said drill:
(c) a data processing and display unit for receiving data about said position and orientation in space of at least said drill from said first three dimensional sensor, for simulating said drill:
(d) a compressed gas unit being connected via a gas line to said dental handpiece, said gas unit providing a compressed gas for rotating said drill, said gas having a flow rate; and
(e) first means for controlling said flow rate of said gas; wherein said data processing and display unit:
  (i) includes a first set of data including said shape, dimensions and fixed location and orientation in space of said artificial tooth;
  (ii) receives a second set of data including said position and orientation in space of at least said drilling end of said drill, from said first three-dimensional sensor:
  (iii) calculates the effect of said position and orientation in space of said drilling end of said drill on said shape of said artificial tooth;
  (iv) displays a simulation of said shape of said artificial tooth, such that a user monitors said effect of said drill on said shape of said artificial tooth by viewing said displayed simulation;
  (v) includes a third set of data, wherein said artificial tooth is simulated as being divided into at least a first simulated region simulating a substance of a first hardness, and a second simulated region simulating a substance of a second hardness said first hardness is harder than said second hardness; and
  (vi) controls said first means for controlling said flow rate of said gas, such that when said drilling end of said drill is at said first simulated region said drill rotates in a first speed, whereas when said drilling end of said drill is at said second simulated region said drill rotates in a second speed, said first speed is slower than said second speed.

9. A simulation system for dentistry comprising:
(a) a hand-held dental handpiece having a drill for drilling a cavity in an artificial tooth having known shape and dimensions and located at a fixed known location and orientation in space, said drill having a drilling end, said dental handpiece being shaped and dimensioned suitable to be held by the hand of a user;
(b) a first three-dimensional sensor attached to said dental handpiece, said first three-dimensional sensor providing the system with position and orientation in space of at least said drill;
(c) a data processing and display unit for receiving data about said position and orientation in space of at least said drill from said first three dimensional sensor, for simulating said drill;
(d) a compressed gas unit being connected via a gas line to said dental handpiece, said gas unit providing a compressed gas for rotating said drill, said gas having a flow rate; and
(e) first means for controlling said/low rate of said gas; wherein said data processing and display unit:
  (i) includes a first set of data including said shape, dimensions and fixed location and orientation in space of said artificial tooth;
  (ii) receives a second set of data including said position and orientation in space of at least said drilling end of said drill, from said first three-dimensional sensor;
  (iii) calculates the effect of said position and orientation in space of said drilling end of said drill on said shape of said artificial tooth;
  (iv) displays a simulation of said shape of said artificial tooth, such that a user monitors said effect of said drill on said shape of said artificial tooth by viewing said displayed simulation;
  (v) includes a third set of data, wherein said artificial tooth is simulated as being divided into at least a first simulated region simulating a substance of a first hardness and a second simulated region simulating a substance of a second hardness, said first hardness is harder than said second hardness, wherein, atmosphere surrounding said artificial tooth is simulated as being a third region of no hardness; and
  (vi) controls said first means for controlling said flow rate of said gas, such that when said drilling end of said drill is at said first simulated region said drill rotates in a first speed, when said drilling end of said chili is at said second simulated region said drill rotates in a second speed, and when said chilling end of said drill is at said third simulated region said drill rotates in a third, speed, said first speed is slower than said second speed, itself slower than said third speed.

10. A simulation system for dentistry comprising:
(a) a hand-held dental handpiece having a drill for drilling a cavity in an artificial tooth having known shape and dimensions, said drill having a drilling end, said dental handpiece being shaped and dimensioned suitable to be held by the hand of a user;
(b) a first three-dimensional sensor attached to said dental handpiece, said first three-dimensional sensor providing the system with position and orientation in space of at least said drill;
(c) a data processing and display unit for receiving data about said position and orientation in space of at least said drill from said first three dimensional sensor, for simulating said drill:
(d) a platform to which said tooth being connected; and
(e) a second three-dimensional sensor being attached to said platform, said second three-dimensional sensor providing the system with position and orientation in space of said artificial moth:

wherein said data processing and display unit:

(i) includes a first set of data including said shape and dimensions of said artificial tooth, said first set of data further including said location and orientation in space of said artificial tooth as received from said second three-dimensional sensor:

(ii) receives a second set of data including said position and orientation in space of at least said drilling end of said drill from said first three-dimensional sensor:

(iii) calculates the effect of said position and orientation in space of said drilling end of said drill on said shape of said artificial tooth; and (iv) displays a simulation of said shape of said artificial tooth, such that a user monitors said effect of said drill on said shape of said artificial tooth by viewing said displayed simulation;

the system further comprising a dental mirror and a third three-dimensional sensor, said third sensor being attached to said dental mirror and providing the system with position and orientation in space of said dental mirror, wherein said data processing and display unit receives from said third three-dimensional sensor a third set of data, said third set of data includes said position and orientation in space of said dental mirror, said data processing and display unit displays a simulation of said dental mirror in space and of a simulated reflection reflected from said displayed simulation of said dental mirror.

11. A simulation system for dentistry as in claim 10, wherein the simulation is scaled-up.

12. A simulation system for dentistry as in claim 10, wherein any of said first and second three-dimensional sensors are selected from the group consisting of electromagnetic based three-dimensional sensors, ultrasound based three-dimensional sensors, optic based three-dimensional sensors and mechanical three-dimensional sensors.

13. A simulation system for dentistry as in claim 10, wherein said platform is a phantom head imitating a head of a human.

14. A simulation system for dentistry, comprising:

(a) a hand-held dental handpiece having a drill for drilling a cavity in an artificial tooth having known shape and dimensions, said drill having a drilling end, said dental handpiece being shaped and dimensioned suitable to be held by the hand of a user;

(b) a first three-dimensional sensor attached to said dental handpiece, said first three-dimensional sensor providing the system with position and orientation in space of at least said drill;

(c) a data processing and display unit for receiving data about said position and orientation in space of at least said drill from said first three dimensional sensor, for simulating said drill;

(d) a platform to which said tooth being connected: and (e) a second three-dimensional sensor being attached to said platform, said second three-dimensional sensor providing the system with position and orientation in space of said artificial tooth:

(f) a compressed gas unit being connected via a gas line to said dental handpiece, said gas unit providing a compressed gas for rotating said drill, said gas having a flow rate;

(g) first means for controlling said flow rate of said gas; wherein said data processing and display unit:

(i) includes a first set of data including said shape and dimensions of said artificial tooth, said first set of data further including said location and orientation in space of said artificial tooth as received from said second three-dimensional sensor:

(ii) receives a second set of data including said position and orientation in space of at least said chilling end of said drill from said first three-dimensional sensor;

(iii) calculates the effect of said position and orientation in space of said drilling end of said drill on said shape of said artificial tooth;

(iv) displays a simulation of said shape of said artificial tooth such that a user monitors said effect of said drill on said shape of said artificial tooth by viewing said displayed simulation:

(v) includes a third set of data, wherein said artificial tooth is simulated as being divided into at least a first simulated region simulating a substance of a first hardness, and a second simulated region simulating a substance of a second hardness, said first hardness is harder than said second hardness; and (vi) controls said first means for controlling said flow rate of said gas, such that when said drilling end of said drill is at said first simulated region said drill rotates in a first speed, whereas when said drilling end of said drill is at said second simulated region said drill rotates in a second speed, said first speed is slower than said second speed.

15. A simulation system for dentistry as in claim 14, wherein said platform is a phantom head imitating a head of a human.

16. A simulation system for dentistry, comprising:

(a) a hand-held dental handpiece having a drill for drilling a cavity in an artificial tooth having known shape and dimensions, said drill having a drilling end, said dental handpiece being shaped and dimensioned suitable to be held by the hand of a user;

(b) a first three-dimensional sensor attached to said dental handpiece, said first three-dimensional sensor providing the system with position and orientation in space of at least said drill;

(c) a data processing and display unit for receiving data about said position and orientation in space of at least said drill from said first three dimensional sensor, for simulating said drill;

(d) a platform to which the tooth being connected; and (e) a second three-dimensional sensor attached to said platform, said second three-dimensional sensor providing the system with position and orientation in space of said artificial tooth;

wherein said data processing and display unit:

(i) includes a first set of data including said shape and dimensions of said artificial tooth, said first set of data further includes said location and orientation in space of said artificial tooth as received from said second three-dimensional sensor;

(ii) receives a second set of data including said position and orientation in space of at least said chilling end of said drill from said first three-dimensional sensor;

(iii) calculates the effect of said position and orientation in space of said drilling end of said drill on said shape of said artificial tooth; and (iv) displays a simulation of said shape of said artificial tooth, such thin a user monitors said effect of said drill on said shape of said artificial tooth by viewing said displayed simulation:

the system further comprising a dental mirror and a third three-dimensional sensor, said third sensor being attached to said dental mirror and providing the system with position and orientation in space of said dental mirror, wherein said data processing and display unit receives from said third three-dimensional sensor a third set of data, said third set of data includes said position and orientation in space of said dental mirror, said data processing and display unit displays a simulation of said dental mirror in space and of a simulated reflection reflected from said displayed simulation of said dental mirror.

17. A simulation system for dentistry as in claim 16, wherein the simulation is scaled-up.

18. A simulation system for dentistry as in claim 16, wherein any of said first and second three-dimensional sensors are selected from the group consisting of electromagnetic based three-dimensional sensors, ultrasound based three-dimensional sensors, optic based three-dimensional sensors and mechanical three-dimensional sensors.

19. A simulation system for dentistry, comprising:

(a) a hand-held dental handpiece having a drill for drilling a cavity in an artificial tooth having known shape and dimensions, said drill having a drilling end, said dental handpiece being shaped and dimensioned suitable to be held by the hand of a user;

(b) a first three-dimensional sensor attached to said dental handpiece, said first three-dimensional sensor providing the system with position and orientation in space of at least said drill;

(c) a data processing and display unit for receiving data about said position and orientation in space of at least said drill from said first three dimensional sensor, for simulating said drill;

(d) a platform to which the tooth being connected; and (e) a second three-dimensional sensor attached to said platform, said second three-dimensional sensor providing the system with position and orientation in space of said artificial tooth;

(f) a compressed gas unit being connected via a gas line to said dental handpiece, said gas unit providing a compressed gas for rotating said drill, said gas having a flow rate;

(g) first means for controlling said flow rate of said gas; wherein said data processing and display unit:

(i) includes a first set of data including said shape and dimensions of said artificial tooth, said first set of data further includes said location and orientation in space of said artificial tooth as received from said second three-dimensional sensor;

(ii) receives a second set of data including said position and orientation in space of at least said drilling end of said drill from said first three-dimensional sensor;

(iii) calculates the effect of said position and orientation in space of said drilling end of said drill on said shape of said artificial tooth; and (iv) displays a simulation of said shape of said artificial tooth, such that a user monitors said effect of said chill on said shape of said artificial tooth by viewing said displayed simulation;

(v) includes third data, wherein said artificial tooth is simulated as being divided into at least a first simulated region simulating a substance of a first hardness and a second simulated region simulating a substance of a second hardness, said first hardness is harder than said second hardness, atmosphere surrounding said artificial tooth is simulated as being a third region of no hardness; and (vi) controls said first means for controlling said flow rate of said gas, such that when said drilling end of said drill is at said first simulated region said drill rotates in a first speed, when said drilling end of said drill is at said second simulated region said drill rotates in a second speed, and when said drilling end of said drill is at said third simulated region said drill rotates in a third speed, said first speed is slower than said second speed, itself slower than said third speed.

20. A simulation system for dentistry, comprising:

(a) a hand-held dental handpiece having a drill for drilling a cavity in a tooth of a patient having a head, said tooth having known shape, dimensions and internal distribution of enamel, dentin and caries affected tissue, said drill having a drilling end, said dental handpiece being shaped and dimensioned suitable to be held by the hand of a user;

(b) a first three-dimensional sensor attached to said dental handpiece, said first three-dimensional sensor providing the system with position and orientation in space of at least said drill;

(c) a data processing and display unit for receiving data about said position and orientation in space of at least said drill from said first three dimensional sensor, for simulating said drill;

(d) a second three-dimensional sensor attached to the head of the patient, said second three-dimensional sensor providing the system with the position and orientation in space of said tooth, said second three-dimensional sensor and said known shape, dimensions and internal distribution of enamel, dentin and caries affected tissue of said tooth being for simulating said tooth by said data processing and display unit, such that a user is capable of monitoring said drilling of said cavity in said tooth;

(e) a dental mirror; and (f) a third three-dimensional sensor, said third three-dimensional sensor being attached to said dental mirror and providing the system with position and orientation in space of said dental mirror, wherein said data processing and display unit receives from said third three-dimensional sensor a set of data, said set of data includes said position and orientation in space of said dental mirror, said data processing and display unit displays a simulation of said dental mirror in space and of a simulated reflection reflected from said displayed simulation of said dental mirror.

21. A simulation system for dentistry as in claim 20, wherein the simulation is scaled-up.

22. A simulation system for dentistry as in claim 20, wherein any of said first and second three-dimensional sensors are selected from the group consisting of electromagnetic based three-dimensional sensors, ultrasound based three-dimensional sensors, optic based three-dimensional sensors and mechanical three-dimensional sensors.

23. A simulation system for dentistry, comprising:

(a) a hand-held dental handpiece having a drill for drilling a cavity in a tooth of a patient having a head, said tooth having known shape, dimensions and internal distribution of enamel, dentin and caries affected tissue, said chill having a drilling end, said dental handpiece being shaped and dimensioned suitable to be held by the hand of a user;

(b) a first three-dimensional sensor attached to said dental handpiece, said first three-dimensional sensor providing the system with position and orientation in space of at least said drill;

(c) a data processing and display unit for receiving data about said position and orientation in space of at least said drill from said first three dimensional sensor, for simulating said drill; and (d) a second three-dimensional sensor attached to the head of the patient, said second three-dimensional sensor providing the system with the position and orientation in space of said tooth said second three-dimensional sensor and said known shape, dimensions and internal distribution of enamel, dentin and caries affected tissue of said tooth being for simulating said tooth by said data processing and display unit, such that a user is capable of monitoring said drilling of said cavity in said tooth;

wherein any of said first and second three-dimensional sensors are selected from the group consisting of electromagnetic based three-dimensional sensors, ultrasound based three-dimensional sensors, optic based three-dimensional sensors and mechanical three-dimensional sensors.

* * * * *